United States Patent [19]
Porter

[11] Patent Number: 5,837,904
[45] Date of Patent: Nov. 17, 1998

[54] FLOWMETER TUBES AND METHOD OF INSTALLING THEM

[75] Inventor: Gary K. Porter, Warrington, Pa.

[73] Assignee: Porter Instrument Company, Inc., Hatfield, Pa.

[21] Appl. No.: 623,418

[22] Filed: Mar. 28, 1996

[51] Int. Cl.$^6$ .......................................................... G01F 1/24
[52] U.S. Cl. .................................. 73/861.56; 128/205.23
[58] Field of Search ........................... 73/861.55, 861.56, 73/861.57; 128/205.23; 339/14, 17; 439/620

[56] References Cited

U.S. PATENT DOCUMENTS

| | | | |
|---|---|---|---|
| 2,389,957 | 11/1945 | Cox | 73/861.57 |
| 2,404,361 | 7/1946 | Brewer | 73/861.57 |
| 2,441,350 | 5/1948 | Fischer | 73/861.57 |
| 2,754,626 | 7/1956 | Porter . | |
| 2,927,829 | 3/1960 | Porter, Jr. . | |
| 3,125,879 | 3/1964 | Porter, Jr. . | |
| 3,914,995 | 10/1975 | Yoshida | 73/861.57 X |
| 4,118,091 | 10/1978 | Frisby | 339/14 |
| 4,558,916 | 12/1985 | Hehl | 339/107 |
| 4,584,997 | 4/1986 | Delong | 128/205.23 |
| 4,603,929 | 8/1986 | Fitzpatrick | 339/17 |
| 5,067,915 | 11/1991 | Kienast | 439/620 |
| 5,402,686 | 4/1995 | Wittman | 73/861.55 |
| 5,507,190 | 4/1996 | Guttmann | 73/861.57 |

OTHER PUBLICATIONS

Blueprint entitled "Tube Indexing Backplate Assembly for a Gas Flowmeter", Porter Instrument Company, Inc. (1976).

*Primary Examiner*—Richard Chilcot
*Assistant Examiner*—Paul D. Amrozowicz
*Attorney, Agent, or Firm*—John F. A. Earley; John F. A. Earley, III; Harding, Earley, Follmer & Frailey

[57] ABSTRACT

A method of preventing the inserting of a wrong flowmeter tube into an anesthesia machine comprises the steps of forming a selected number of longitudinal ridges at selected places on the inside surface of an upper portion of a flowmeter tube, attempting to insert the upper end portion into a socket pin mounted on the housing of a anesthesia machine, seating the tube on the socket pin if the socket pin exterior surface has grooves corresponding to the number and placement of ridges on the flowmeter tube, and rejecting the tube by the socket pin if the socket pin exterior surface does not have grooves corresponding to the number and placement of the ridges on the flowmeter tube, since the lack of said correspondences indicates that the tube is the wrong tube for the socket pin. A flowmeter measuring tube for medical applications such as anesthesia machines has a selected number of ridges extending inwardly from the inside surface of the flowmeter tube from an upper end portion, said number of ridges being adapted to slide into a like number and position of grooves in a socket pin of a housing of an anesthesia machine for holding the tube in place, whereby the ridges of the flowmeter tube and the grooves of the socket pin provide a safety feature that prevents the insertion of the wrong tube into the socket pin.

8 Claims, 4 Drawing Sheets

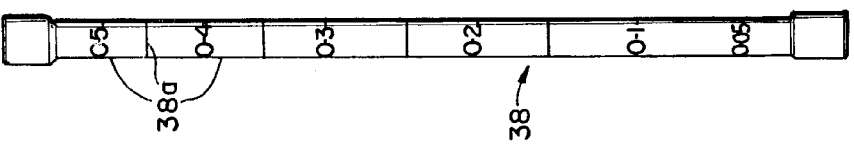
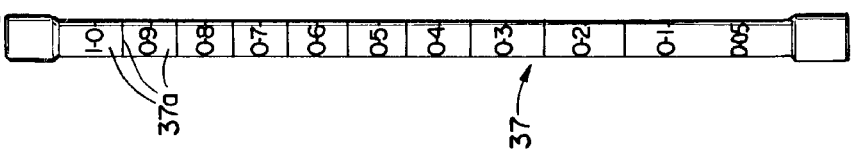
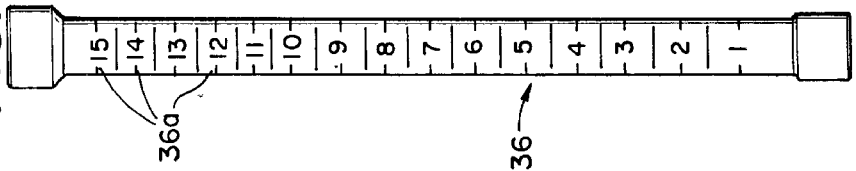
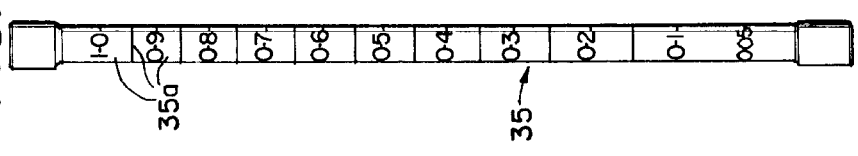
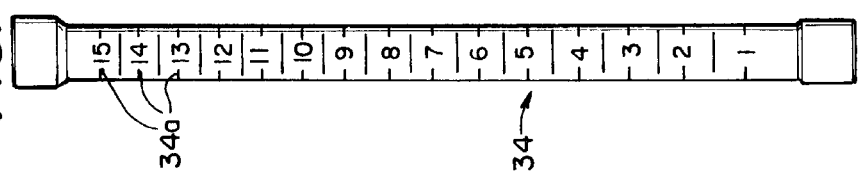
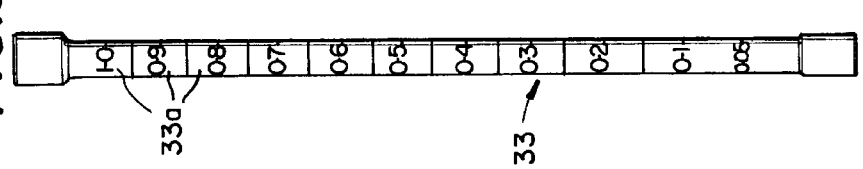
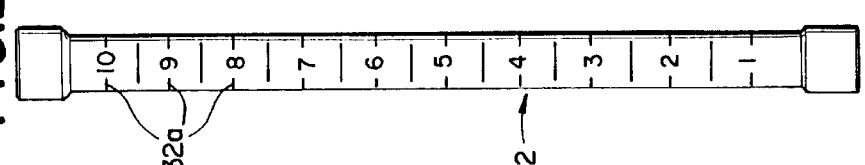
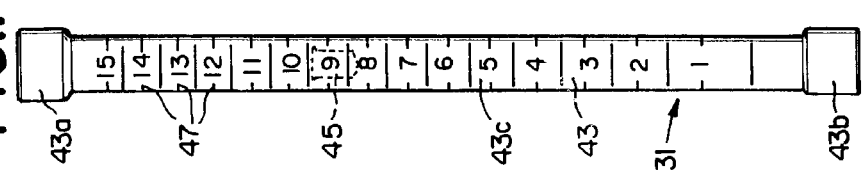
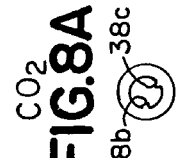

FLOWMETER TUBES AND METHOD OF INSTALLING THEM

BACKGROUND OF THE INVENTION

1. Field of the Invention

This invention relates to flowmeter tubes for anesthesia equipment, and more particularly concerns flowmeter tubes and method for insuring that a wrong flowmeter tube cannot be inserted into an incorrect position in an anesthesia machine.

2. Description of the Prior Art

During an operation on a patient, whether it be for appendicitis or for some other problem, the patient is anesthetized and is fed various gases in order to keep him unconscious, alive and well during the operation. Such gases may include $HeO_2$, $N_2O$, $O_2$, air, and $CO_2$. The flow of such gases is carefully watched and closely monitored so that the patient receives the correct amounts of each. The rate of gas flow is indicated by flowmeter glass tubes which have calibrated markings on them or adjacent to them. A float in the tube is impinged upon by the flowing gas and its position in the tube indicates the amount of the gas flowing through the tube.

The inside surface of each flowmeter glass tube is tapered from its lower portion to its upper portion so that the upper portion is wider than the lower portion. As the gas flow increases, it pushes the float upwardly in the tube and gas flows through an annular opening created between the float and the inside surface of the tube. The float is read against the graduated markings of the tube to measure the gas flow.

These flowmeter tubes are put into banks of tubes, for example, 5 to 7 different tubes. The tubes come in different sizes because the amount of flow of the various gases is different. One size tube may handle flow rates from 50 ccs a minute to 150 ccs, and another size tube may handle flow rates from 1 liter to 10 liters per minute.

In a bank of flowmeter tubes, there may be tubes to indicate the flow rate of oxygen, nitrous oxide, air, helium, carbon dioxide, and water, for example.

It has been a problem, especially in the field, to prevent a field service person from replacing a tube with the wrong tube so that the gas flow in the tube is measured incorrectly. The consequences of inserting a wrong tube could be disastrous. For example, if a patient undergoing surgery for appendicitis were supplied with an overdose of the anesthetic because of the insertion of a wrong tube in the anesthesia machine, he could suffer cardiac arrest and die.

In a flowmeter tube, the gas enters the bottom of the tube and the molecules of the gas strike the float and force it upwardly in the tube and as it rises, the annular area between the float and the inside surface of the tube increases to allow more gas flow to pass. This gives a very accurate measure of the flow rate of the gas.

A flowmeter gas tube may be made by putting a glass tube around a mandrel, drawing a vacuum on the inside of the glass tube, and progressively heating the glass tube until the glass shrinks onto the mandrel, thus providing the desired taper on the inside surface of the glass tube.

If it is desired to make the upper and lower portions of the tube into a bell shape, a mandrel may be supplied having a bell shaped top portion, a tapered middle portion, and a separate bell-shaped lower portion may be added to the bottom of the tapered mandrel to produce a flowmeter tube having bell shaped portions at each end joined together by a tapered middle portion.

SUMMARY OF THE INVENTION

It is an object of this invention to provide flowmeter tubes that prevent the insertion of a wrong flowmeter tube in an incorrect position in an anesthesia machine.

The object of the invention is accomplished by providing a flowmeter tube having selected longitudinal ridges which are formed in at least one of the upper and lower portions of the flowmeter tube on the inside surface of the tube. The number and positions of the selected ridges correspond to a selected gas and graduation markings on the tube, and also correspond to selected longitudinal grooves in socket pins in the anesthesia machine.

For example, the longitudinal grooves in a socket pin for oxygen may accept the ridges of an oxygen flowmeter tube, but do not accept the ridges of a nitrous oxide flowmeter tube, so that a nitrous oxide flowmeter tube cannot be inserted onto an oxygen socket pin by mistake.

BRIEF DESCRIPTION OF THE DRAWINGS

FIG. 1 is a view in elevation of a flowmeter tube constructed in accordance with this invention that is adapted for passing $HeO_2$;

FIG. 1A is a view in top plan of the flowmeter tube of FIG. 1;

FIG. 2 is a view in elevation of a flowmeter tube for $N_2O$;

FIG. 2A is a view in top plan of the flowmeter tube of FIG. 2;

FIG. 3 is a view in elevation of a flowmeter tube for $N_2O$ which is smaller in diameter than the flowmeter tube of FIG. 2;

FIG. 3A is a view in top plan of the flowmeter tube of FIG. 3;

FIG. 4 is a view in elevation of a flowmeter tube for $O_2$;

FIG. 4A is a view in top plan of the flowmeter tube of FIG. 4;

FIG. 5 is a view in elevation of a flowmeter tube for $O_2$ which is smaller in diameter than the tube of FIG. 4;

FIG. 5A is a view in top plan of the tube of FIG. 5;

FIG. 6 is a view in elevation of a flowmeter tube for air;

FIG. 6A is a view in top plan of the tube of FIG. 6;

FIG. 7 is a view in elevation of a tube for air which is smaller in diameter than the tube of FIG. 6;

FIG. 7A is a view in top plan of the flowmeter tube of FIG. 7;

FIG. 8 is a view in elevation of a flowmeter tube for $CO_2$;

FIG. 8A is a view in top plan of the tube of FIG. 8;

DETAILED DESCRIPTION

Figure 9:
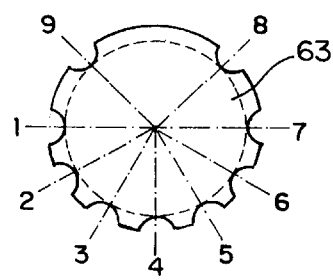
FIG. 9 is a view in plan of a mandrel showing selected groove positions from 1 through 9, any two or more of which may be selected to make and identify a selected flowmeter tube for a selected gas, and distinguish it from other flowmeter tubes which are adapted for different gases.

Turning now to the drawings, flowmeter tubes 31 through 38 are shown that are constructed in accordance with this invention. These are flowmeter measuring tubes for use in medical applications such as in anesthesia machines to measure the flow of gases as they are being fed to a patient undergoing an operation. The flowmeter measuring tubes 31 through 38 are used to control the flow of $HeO_2$, $N_2O$, $O_2$, air, and $CO_2$, for example.

Referring now more specifically to flowmeter tube 31 shown in FIGS. 1 and 1A, flowmeter tube 31 has an elongated glass tube 43 with an upper portion 43a connected to a lower portion 43b by a middle portion 43c having an inside surface 43d. The upper portion 43a and lower portion 43b are bell shaped, and the diameter of upper portion 43a is larger than the diameter of lower portion 43b.

The middle portion 43c has a taper which tapers outwardly from the lower portion 43b to the upper portion 43a.

A float 45 inside the glass tube 43 rises and falls in accordance with the force of the gas which enters the tube from the lower portion 43b.

The float 45 is read against graduated markings 47 on middle portion 43c to measure the position of the float 45 and to give an accurate indication of the gas flow through the flowmeter tube 31.

A selected number of ridges 49, 51 extend inwardly from the inside surface 43d of the tube 43 at position 1 and 3 at the upper portion 43a. Similar ridges may also extend inwardly from the lower portion 43b, but this is not necessary and it is more expensive to line up ridges at the top and bottom.

The elongated ridges 49, 51 are adapted to slide into a selected like number and position of elongated grooves 53, 55 at positions 1 and 3 in a socket pin 57 (FIG. 29) for holding the flowmeter tube 31 in place in an anaesthesia machine.

Since the selected ridges 49, 51 for the flowmeter tube 31 are unique in their number and placement, and the grooves 53, 55 of the pin socket 57 match ridges 49 and 51 and do not match the ridges of any other flowmeter tube 32 to 38, there is provided a safety feature that prevents insertion of the tube 31 into a wrong socket.

In operation, the method of this invention of preventing insertion of the wrong flowmeter tube into an anaesthesia machine comprises taking an elongated glass tube, placing it around a mandrel, and subjecting it to a vacuum while heating it to form it into the tapered shape of a flowmeter tube such as flowmeter tube 31 with bell shaped upper end portion 43a connected to a bell shaped lower end portion 43b by a tapered middle portion 43c so that the inside surface 43d of the middle portion 43c is wider at the upper end portion 43a than at the lower end portion 43b. The mandrel has an upper bell and middle taper portion extending downwardly therefrom into a separate bell-shaped lower portion which provides for removing the mandrel from the tapered tube, since the upper bell and middle taper portion may be pulled upwardly, and the separate lower portion may be pulled downwardly from the formed tube.

A selected number of longitudinal ridges 49, 51 are formed at selected positions 1 and 3 on the inside surface 43d of the upper end portion 43a.

A float 45 is placed inside the tube 43, and graduated markings 47 are placed on the tube 43 which measure the position of the float 45 in the tube 43.

A socket pin 57 extends downwardly from a base 57c of an anaesthesia machine, and the socket pin 57 has been provided with a selected number and position of longitudinal grooves 53, 55 at positions 1 and 3. If the grooves 53, 55 of the socket pin 57 are matched by the ridges 49, 51 of the flowmeter tube 31, the tube 31 can be inserted onto the socket pin 57.

If the number and placement of ridges 49, 51 do not correspond to the number and placement of grooves 53, 55 in socket pin 57, the tube is rejected by the socket pin 57, since the lack of correspondence between the ridges and the grooves is an indication that the tube 31 is the wrong tube for the socket pin 57.

FIG. 2 shows a flowmeter tube 32 for $N_2O$ and is provided with graduated markings 32a and longitudinal ridges 32b, 32c at positions 1 and 7 as shown in mandrel 63 in FIG. 9.

Figure 20:
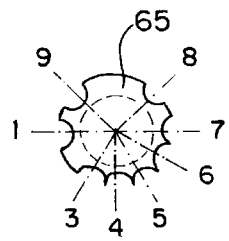
FIG. 20 is a view in plan of a smaller mandrel which illustrates longitudinal groove positions 1 through 9 with the exception of position 2 which has been omitted because the mandrel of FIG. 20 is smaller than the mandrel of FIG. 10, and practical conditions of machining make it difficult to include position 2 in the choice of grooves of this smaller size mandrel and smaller size flowmeter tubes because position 2 is so close to position 1.

FIG. 3 shows a smaller flowmeter tube 33 for $N_2O$ with graduated markings 33a and longitudinal ridges 33b and 33c at positions 1 and 7 as shown in mandrel 65 of FIG. 20.

Figure 10:
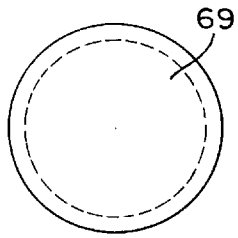
FIG. 10 is a view in plan of a mandrel with no grooves as yet being formed on its side surfaces.

FIG. 4 shows flowmeter tube 34 for $O_2$ with graduated markings 34a and longitudinal ridges 34b and 34c at positions 1 and 9 as shown in mandrel 63 of FIG. 10.

Figure 30:
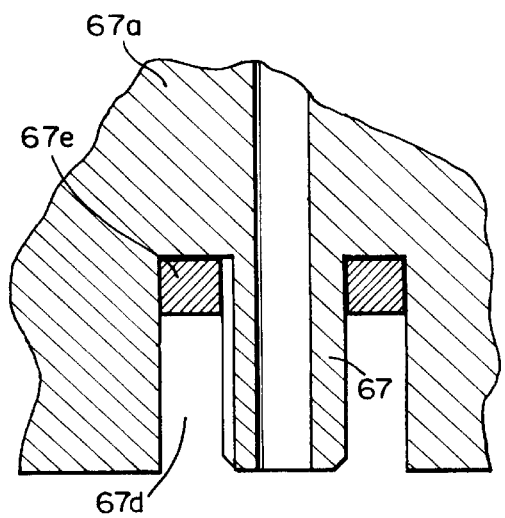
FIG. 30 is a view in section of a socket pin adapted to receive a selected flowmeter tube of smaller type.
Figure 29A:
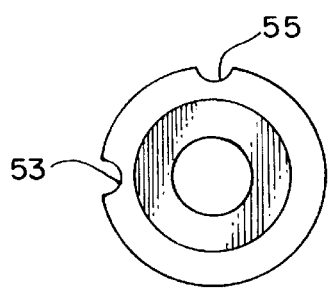
FIG. 29A is a view in plan of the socket pin of FIG. 29 and shows the grooves at positions 1 and 4, so that the pin socket is adapted to receive flowmeter tubes having longitudinal ridges at these positions.
Figure 30A:
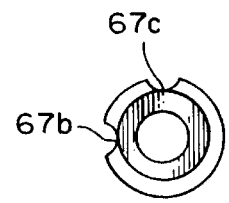
FIG. 30A is a view in plan of the socket pin of FIG. 30 and shows grooves at positions 1 and 4.

FIG. 5 shows a smaller oxygen flowmeter tube 35 with graduated markings 35a and ridges 35b and 35c at positions 1 and 9 as shown in smaller mandrel 65 in FIG. 20. The smaller flowmeter tube 33 fits onto a socket pin 67 (FIG. 30) which extends downwardly from a base 67a of an anesthesia machine. Socket pin 67 has been provided with a selected number and position of longitudinal grooves 67b, 67c at positions 1 and 9. Base 67a forms an annular groove 67d around pin 67 and a sealing ring 67e sits in the base of the annular groove 67d. If the grooves 67b, 67c of the socket pin 67 are matched by the ridges 35b, 35c of flowmeter tube 35, the tube 35 can be inserted onto the socket pin 67.

If the number and placement of ridges of the flowmeter tube do not correspond to the number and placement of the grooves in the socket pin 67, the tube is rejected by the socket pin.

Also, if it were attempted to insert a larger tube 34 (FIG. 4), which is for $O_2$ and has the same ridges as tube 35, instead of smaller tube 35 (FIG. 5) onto socket pin 67, the tube 34 would be rejected by socket pin 67 even though there was correspondence between grooves and ridges because annular groove 67d would reject the larger outside diameter of the larger flowmeter tube 34.

FIG. 6 shows flowmeter tube 36 for air with its graduated markings 36a and with longitudinal ridges 36b, 36c at positions 1 and 8 as shown in mandrel 63 of FIG. 9.

FIG. 7 shows smaller flowmeter tube 37 for air with its graduated markings 37a and its longitudinal ridges 37b and 37c at positions 1 and 8 as shown on smaller mandrel 65 in FIG. 20.

FIG. 8 shows smaller flowmeter tube 38 for $CO_2$ with its graduated markings 38a and its longitudinal ridges 38b and 38c at positions 1 and 5 as shown in mandrel 65 of FIG. 20.

FIG. 9 is a plan view of mandrel 63 and shows longitudinal groove positions 1 through 9. Positions 1 through 7 are separated from each other by 30°, position 7 is separated from position 8 by 45°, position 8 is separated from position 9 by 90°, and position 9 is separated from position 1 by 45°. Position 1 corresponds to 9 o'clock on a clockface, position 2 corresponds to 8 o'clock, position 3 corresponds to 7 o'clock, position 4 corresponds to 6 o'clock, position 5 corresponds to 5 o'clock, position 6 corresponds to 4 o'clock, position 7 corresponds to 3 o'clock, position 8 corresponds to half past 1 o'clock, and position 9 corresponds to half past 10 o'clock.

FIG. 10 is a plan view of a mandrel 69 that is not provided with any longitudinal grooves.

Figure 11:
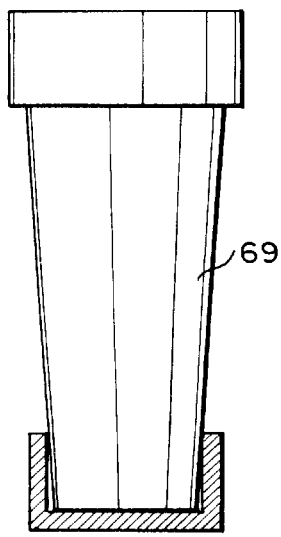
FIG. 11 is a view in elevation of the mandrel of FIG. 11.

FIG. 11 is a view in elevation of the mandrel 69 of FIG. 10.

Figure 12:
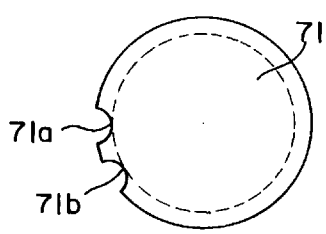
FIG. 12 is a view in plan of mandrel with longitudinal grooves formed in positions 1 and 2.

FIG. 12 is a plan view of a mandrel 71 with longitudinal groove 71a at position 1 and longitudinal groove 71b at position 2 which is 30° from groove 71a.

Figure 13:
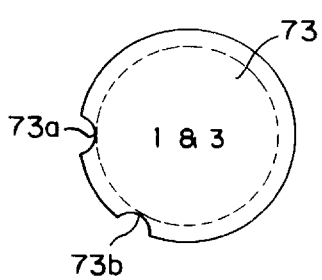
FIG. 13 is a view in plan of a mandrel with longitudinal grooves at positions 1 and 3 which are the positions selected for heliox.

FIG. 13 is a plan view of mandrel 73 with a longitudinal groove 73a at position 1 and a longitudinal groove 73b at position 3, and this mandrel 73 is used to make flowmeter tubes for heliox like tube 31 of FIG. 1.

Figure 14:
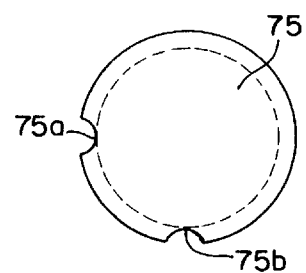
FIG. 14 is a view in plan of a mandrel with longitudinal grooves formed at positions 1 and 4.

FIG. 14 is a plan view of a mandrel 75 with a longitudinal groove 75a at position 1 and a longitudinal groove 75b at position 4.

Figure 15:
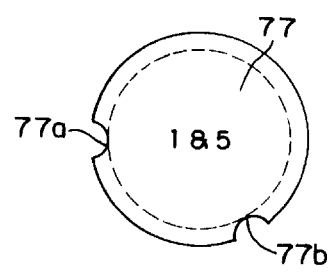
FIG. 15 is a view in plan of a mandrel with longitudinal grooves at positions 1 and 5 which have been selected for carbon dioxide.

FIG. 15 is a plan view of a mandrel 77 with a longitudinal groove 77a at position 1 and a longitudinal groove 77b at position 5. Mandrel 77 is used to make flowmeter tubes for carbon dioxide.

Figure 16:
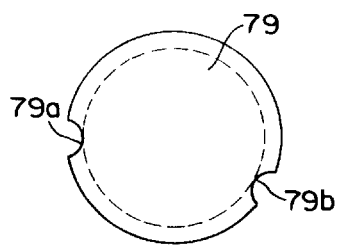
FIG. 16 is a view in plan of a mandrel showing longitudinal grooves at positions 1 and 6.

FIG. 16 is a plan view of a mandrel 79 with a longitudinal groove 79a at position 1 and a longitudinal groove 79b at position 6. The side walls of groove 79a are shown as being at an angle of 120° to each other, but may be varied from an angle somewhat greater than 0° to an angle of 180°, which would produce a flat surface instead of a groove.

Figure 17:
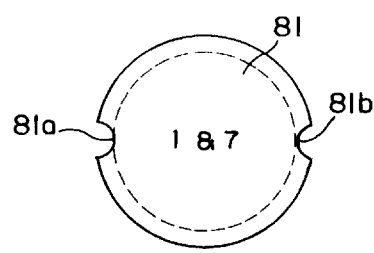
FIG. 17 is a view in plan of a mandrel having longitudinal grooves at positions 1 and 7 which have been selected for nitrous oxide.

FIG. 17 is a plan view of a mandrel 81 having a longitudinal groove 81a at position 1 and a longitudinal groove 81b at position 7 for use in producing flowmeter tubes for nitrous oxide, such as flowmeter tube 32 in FIG. 2.

Figure 18:
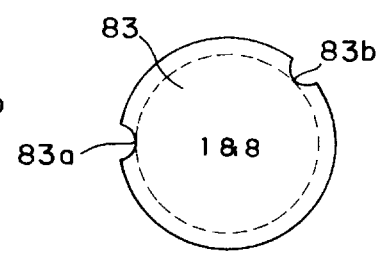
FIG. 18 shows a view in plan of a mandrel with longitudinal grooves at positions 1 and 8 which have been selected for air.

FIG. 18 is a plan view of a mandrel 83 with a longitudinal groove 83a at position 1 and a longitudinal groove 83b at position 8 and is used to make flowmeter tubes for air, such as flowmeter tube 36 shown in FIG. 6.

Figure 19:
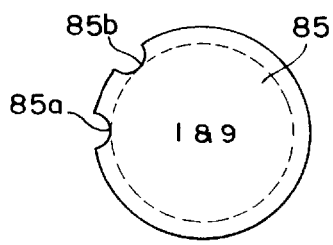
FIG. 19 shows a view in plan of a mandrel having longitudinal grooves at positions 1 and 9 which have been selected for oxygen.

FIG. 19 is a plan view of a mandrel 85 which has a groove 85a at position 1 and a groove 85b at position 9 and is used to produce flowmeter tubes for oxygen such as flowmeter tube 34 shown in FIG. 4.

FIG. 20 is a plan view of a mandrel 65 and shows grooves at position 1 and positions 3 through 9. Position 2 is omitted from mandrel 65 because of the difficulty in machining a longitudinal groove 2 so close to position 1 on such a small mandrel.

Figure 21:
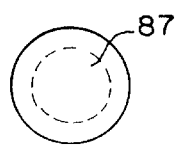
FIG. 21 is a view in plan of a smaller mandrel without any longitudinal grooves.

FIG. 21 is a plan view of a mandrel 87 which does not have any longitudinal grooves. Mandrel 87 is not used in forming the flowmeter tubes of this invention, but illustrates a mandrel before any longitudinal grooves are cut into it.

Figure 22:
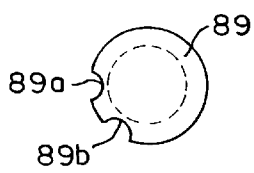
FIG. 22 is a view in plan of a smaller mandrel with longitudinal grooves at positions 1 and 3.

FIG. 22 is a plan view of a mandrel 89 with a longitudinal groove 89a at position 1 and a longitudinal groove 89b at position 3.

Figure 23:
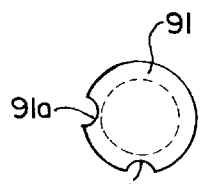
FIG. 23 is a view in plan of a smaller mandrel with longitudinal grooves at positions 1 and 4.

FIG. 23 is a plan view of a mandrel 91 with a longitudinal groove 91a at position 1 and a longitudinal groove 91b at position 4.

Figure 24:
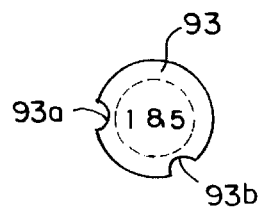
FIG. 24 is a plan view of a smaller mandrel with grooves at positions 1 and 5 which have been selected to identify carbon dioxide.

FIG. 24 is a plan view of mandrel 93 with a longitudinal groove 93a at position 1 and a longitudinal groove 93b at position 5 and is used in making a flowmeter tube for carbon dioxide such as flowmeter tube 38 of FIG. 8.

Figure 25:
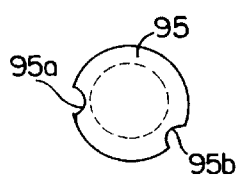
FIG. 25 is a plan view of a smaller mandrel showing grooves at positions 1 and 6.

FIG. 25 is a plan view of a mandrel 95 with a longitudinal groove 95a at position 1 and longitudinal groove 95b at position 6.

Figure 26:
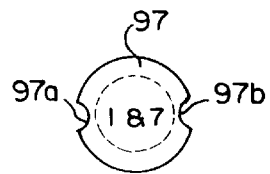
FIG. 26 is a plan view of a smaller mandrel with grooves at positions 1 and 7 which have been selected to identify nitrous oxide.

FIG. 26 is a plan view of a mandrel 97 with a longitudinal groove 97a at position 1 and a longitudinal groove 97b at position 7 and is used in making flowmeter tubes for nitrous oxide such as smaller tube 33 shown in FIG. 3.

Figure 27:
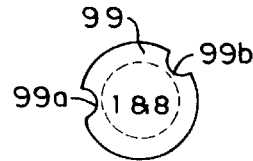
FIG. 27 is a plan view of a smaller mandrel with grooves at positions 1 and 8 which have been selected to identify air.

FIG. 27 is a plan view of a mandrel 99 with a longitudinal groove 99a at position 1 and a longitudinal groove 99b at position 8 and is used to make flowmeter tubes for air such as smaller flowmeter tube 37 shown in FIG. 7.

Figure 28:
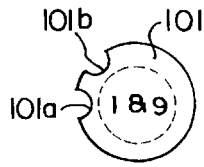
FIG. 28 is a plan view of a smaller mandrel having grooves at positions 1 and 9 which have been selected to identify oxygen.

FIG. 28 is a plan view of a mandrel 101 with a longitudinal groove 101a at position 1 and longitudinal groove 101b at position 9 and is used to make flowmeter tubes for oxygen such as smaller tube 35 shown in FIG. 5.

Figure 29:
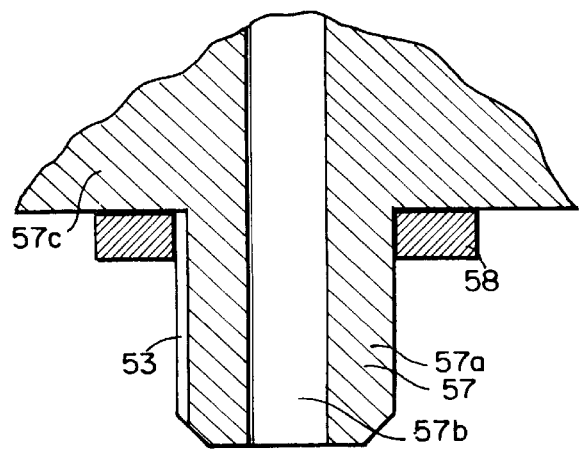
FIG. 29 is a view in section of a socket pin adapted to receive a selected flowmeter tube of the larger type.

FIG. 29 is a view in vertical cross section of a socket pin 57 with a pin portion 57a having a gas passageway 57b and a base portion 57c of the housing of the anesthesia machine. A resilient annular gasket 105 sits on base portion 57c around pin portion 57a to seal the end of the tube. Pin portion 57a includes a longitudinal groove 53 at position 1 and a longitudinal groove 55 at position 4.

The groove positions from 1 to 9 have been selected arbitrally, with positions 1 through 7 being 30° from each other, and position 8 being 45° from position 7, and position 9 being 90° from position 8 and 45° from position 1.

The diameter of upper end portion 43a must be larger than the upper diameter of the tapered portion of the middle portion 43c. Also, the diameter of the lower end portion 43b must be larger than the diameter of the lower end of the tapered middle portion 43c.

The upper end portion 43a may be provided with appropriate longitudinal ridges, or the lower end portion 43b may be provided with appropriate longitudinal ridges, but the upper ridges are presently preferred.

Instead of grinding the side walls of the mandrel grooves so that the side walls 120° apart, the side walls could be 180° apart so that the resulting indexing groove is a ground flat.

It is realized that the object of preventing insertion of the wrong flowmeter tube onto a socket pin of an anesthesia machine may be accomplished by a reversal of parts by forming the grooves on the inside surface of the tubes, and forming the ridges on the mandrel and on the socket pins of an anesthesia machine. Accordingly, in the claims the word "ridges" is defined as including "grooves", where appropriate, and vice versa, the word "grooves" is defined as including the word "ridges", where appropriate.

I claim:

1. A method of preventing the inserting of a wrong flowmeter tube into an anesthesia machine comprising taking an elongated glass tube, forming it into a flowmeter tube with an upper end portion connected to a lower end portion by a middle portion with an inside surface, forming the upper end portion and the lower end portion into a bell shape, forming a taper (59) on the inside surface (43d) of the middle portion (43c) so that the inside surface (43d) of the middle portion (43c) is wider at the upper end portion than at the lower end portion, placing a float (45) inside the tube (43), placing graduated markings (61) on or adjacent to the tube (43) which measure the position of the float (45) in the tube (43), forming a selected number of longitudinal ridges at selected places on the inside surface of an end portion of the tube to form a ridged end portion, attempting to insert said ridged end portion of the tube onto a socket pin mounted on a housing of the anesthesia machine, seating the tube on the socket pin if the socket pin exterior surface has grooves corresponding to the number and placement of said tube ridges, and rejecting the tube by the socket pin if the socket pin exterior surface does not have grooves corresponding to the number and placement of said ridges on the flowmeter tube since the lack of said correspondence indicates that the tube is the wrong tube for the socket pin.

2. The method of claim 1, including selecting two ridges as the selected number of ridges, selecting a position 1 which is at 9 o'clock on a clockface for the position of one of the ridges, and selecting a position 7 which is at 3 o'clock on a clockface for the position of the other ridge.

3. In a method of preventing the inserting of a wrong flowmeter tube into an anesthesia machine which includes taking an elongated glass tube, forming it into a flowmeter tube with an upper end portion connected to a lower end portion by a middle portion with an inside surface, forming the upper end portion and the lower end portion into a bell shape, forming a taper (59) on the inside surface (43d) of the middle portion (43c) so that the inside surface (43d) of the middle portion (43c) is wider at the upper end portion than at the lower end portion, placing a float (45) inside the tube (43), placing graduated markings on the tube (43) which measure the position of the float (45) in the tube (43), the steps comprising:

forming a selected number of longitudinal ridges at selected positions on the inside surface of an end portion of the tube to form a ridged end portion of the tube, attempting to insert the said ridged end portion of the tube onto a socket pin on a housing of an anesthesia machine, seating the tube on the socket pin if the socket pin exterior surface has grooves corresponding to the number and placement of said ridges on the flowmeter tube, and rejecting the tube by the socket pin if the socket pin exterior surface does not have grooves corresponding to number and placement of said ridges on the flowmeter tube since the lack of said correspondence indicates that the tube is the wrong tube for the socket pin.

4. The method of claim 3, including selecting two ridges as the selected number of ridges, selecting a position 1 which is at 9 o'clock on a clockface for the position of one of the ridges, and selecting a position 7 which is at 3 o'clock on a clockface for the position of the other ridge.

5. A flowmeter measuring tube for medical applications such as anesthesia machines comprising an elongated glass tube (43) having an upper portion (43a) connected to a lower portion (43b) by a middle portion (43c) having an inside surface (43d), said upper portion and said lower portion having a bell shape, said middle portion (43c) having a taper on its inside surface which tapers outwardly from said lower portion (43b) to upper portion (43a), a float (45) inside the glass tube (43) which rises and falls in accordance with the force of a gas which enters the tube from the lower portion (43b), graduated markings (47) on the middle portion (43c) of the tube (43) which measure the position of the float (45), and a selected number of ridges extending inwardly from the inside surface of an end portion of the tube at selected positions, said number of ridges being adapted to slide into a like number and position of grooves in a socket pin of a housing of an anesthesia machine for holding the tube in place, whereby the ridges of the flowmeter tube and the grooves of the socket pin provide a safety feature that prevents the insertion of the wrong tube onto the socket pin.

6. The flowmeter measuring tube of claim 5, wherein the selected number of ridges is two and the selected positions for one of the ridges is at position 1 which is at 9 o'clock on a clockface, and the selected position for the other ridge is at position 7 which is at 3 o'clock on a clockface.

7. In a flowmeter measuring tube for medical applications such as anesthesia machines comprising an elongated glass tube (43) having an upper portion (43a) connected to a lower portion (43b) by a middle portion (43c) having an inside surface (43d), said upper and lower portions having a bell shape, said middle portion (43*c*) having a taper on its inside surface which tapers outwardly from said lower portion (43*b*) to upper portion (43*a*), a float (45) inside the glass tube (43) which rises and falls in accordance with the force of a gas which enters the tube from the lower portion (43*b*), graduated markings (47) on the middle portion (43*c*) of the tube (43) which measure the position of the float (45), the improvement comprising a selected number of ridges extending inwardly from the inside surface of an end portion of the tube, a socket pin having an outside surface, a selected number of grooves formed in the outside surface of the pin, said number of ridges being adapted to slide into a like number and position of grooves in a socket pin of a housing of an anesthesia machine for holding the tube in place, whereby the ridges of the flowmeter tube and the grooves of the socket pin provide a safety feature that prevents the insertion of the wrong tube onto the socket pin.

8. The flowmeter measuring tube of claim 7, wherein the selected number of ridges is two and the selected positions for one of the ridges is at position 1 which is at 9 o'clock on a clockface, and the selected position for the other ridge is at position 7 which is at 3 o'clock on a clockface.

\* \* \* \* \*